(12) United States Patent
Afzali-Azdakani et al.

(10) Patent No.: US 8,598,018 B2
(45) Date of Patent: Dec. 3, 2013

(54) FORMING AN ELECTRODE HAVING REDUCED CORROSION AND WATER DECOMPOSITION ON SURFACE USING A CUSTOM OXIDE LAYER

(75) Inventors: Ali Afzali-Azdakani, Ossining, NY (US); Shafaat Ahmed, Yorktown Heights, NY (US); Hariklia Deligianni, Tenafly, NJ (US); Dario L. Goldfarb, Dobbs Ferry, NY (US); Stefan Harrer, New York, NY (US); Hongbo Peng, Yorktown Heights, NY (US); Stanislav Polonsky, Putnam Valley, NY (US); Stephen Rossnagel, Pleasantville, NY (US); Xiaoyan Shao, Yorktown Heights, NY (US); Gustavo A. Stolovitzky, Riverdale, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 12/820,487

(22) Filed: Jun. 22, 2010

(65) Prior Publication Data

US 2011/0312164 A1 Dec. 22, 2011

(51) Int. Cl.
*H01L 21/20* (2006.01)
*H01L 21/36* (2006.01)
*H01L 21/283* (2006.01)

(52) U.S. Cl.
USPC ........... 438/483; 438/104; 438/478; 438/758; 438/768; 438/770; 257/E21.09; 257/E21.159; 257/E21.461

(58) Field of Classification Search
USPC .................. 438/104, 478, 479, 483, 485, 488, 438/768–770, 779, 787–789, 798; 257/E21.09, E21.159, E21.461
See application file for complete search history.

(56) References Cited

U.S. PATENT DOCUMENTS

| 4,389,371 A | 6/1983 | Wilson et al. |
| 5,795,782 A | 8/1998 | Church et al. |
| 6,352,838 B1 | 3/2002 | Krulevitch et al. |
| 6,627,067 B1 * | 9/2003 | Branton et al. ............... 205/778 |

(Continued)

FOREIGN PATENT DOCUMENTS

| WO | WO-0036407 | 6/2000 |
| WO | WO-0181896 | 11/2001 |

(Continued)

OTHER PUBLICATIONS

Totta, "In-process intergranular corrosion in Al alloy thin films", Journal of Vacuum Science and Technology, vol. 13, Issue: 1, 1976, pp. 26-27.

(Continued)

*Primary Examiner* — Julio J Maldonado
*Assistant Examiner* — Daniel Shook
(74) *Attorney, Agent, or Firm* — Cantor Colburn LLP; Vazken Alexanian

(57) ABSTRACT

The present invention provides a method of forming an electrode having reduced corrosion and water decomposition on a surface thereof. A conductive layer is deposited on a substrate. The conductive layer is partially oxidized by an oxygen plasma process to convert a portion thereof to an oxide layer thereby forming the electrode. The oxide layer is free of surface defects and the thickness of the oxide layer is from about 0.09 nm to about 10 nm and ranges therebetween, controllable with 0.2 nm precision.

27 Claims, 4 Drawing Sheets

(56) References Cited

U.S. PATENT DOCUMENTS

| | | | |
|---|---|---|---|
| 6,682,659 B1 * | 1/2004 | Cho et al. ..................... | 216/13 |
| 6,716,620 B2 | 4/2004 | Bashir et al. | |
| 6,905,586 B2 | 6/2005 | Lee | |
| 7,238,485 B2 | 7/2007 | Akeson et al. | |
| 7,279,337 B2 | 10/2007 | Zhu | |
| 7,347,921 B2 * | 3/2008 | Barth et al. ................ | 204/451 |
| 7,468,271 B2 | 12/2008 | Golovchenko | |
| 7,625,706 B2 | 12/2009 | Akeson et al. | |
| 8,003,319 B2 | 8/2011 | Polonsky et al. | |
| 2002/0088712 A1 | 7/2002 | Miles | |
| 2003/0085719 A1 | 5/2003 | Yoon et al. | |
| 2003/0161951 A1 * | 8/2003 | Yuan et al. ............... | 427/255.28 |
| 2004/0011650 A1 | 1/2004 | Zenhausern et al. | |
| 2004/0163955 A1 | 8/2004 | Miles et al. | |
| 2006/0019259 A1 | 1/2006 | Joyce | |
| 2006/0057585 A1 | 3/2006 | McAllister | |
| 2006/0068401 A1 | 3/2006 | Flory | |
| 2006/0210990 A1 * | 9/2006 | Todd et al. ..................... | 435/6 |
| 2008/0187915 A1 * | 8/2008 | Polonsky et al. ................ | 435/6 |
| 2009/0038938 A1 | 2/2009 | Mezic et al. | |
| 2009/0093376 A1 | 4/2009 | Wo et al. | |
| 2010/0025249 A1 | 2/2010 | Polonsky et al. | |
| 2010/0112667 A1 | 5/2010 | Sundaram et al. | |

FOREIGN PATENT DOCUMENTS

| | | |
|---|---|---|
| WO | WO-2006027780 | 3/2006 |
| WO | WO-PCTEP08050562 | 5/2008 |
| WO | WO-2008092760 A1 | 8/2008 |

OTHER PUBLICATIONS

Schmutz, et al., Corrosion Studies with the Atomic Force Micorscope, Part I: Characterization of Potential Inhomogeneities on Passive Surfaces by Surface Potential Imaging, 2005 Veeco Instruments Inc.

U.S. Appl. No. 12/820,516, Afzali-Ardakani, et al.

U.S. Appl. No. 12/820,543, Afzali-Ardakani, et al.

U.S. Appl. No. 12/820,574, Afzali-Ardakani, et al.

J. Li et al., "Ion-Beam Sculpting at Nanometre Length Scales," Macmillan Magazines Ltd., Nature, Jul. 2001, pp. 166-169, vol. 412.

A.J. Storm et al., "Translocation of Double-Strand DNA Through a Silicon Oxide Nanopore," The American Physical Society, Physical Review, 2005, pp. 1-10, E71.

Habib, et al., "Atmospheric oxygen plasma activation of silicon (100) surfaces", Journal of Vacuum Science Technology, May/Jun. 2010.

Kakiuchi, et al., "Highly efficient oxidation of silicon at low temperatures using atmospheric pressure plasma", Appl. Phys. Lett. 90, 091909 (2007).

Han, et al., "Oxygen plasma treatment of gate metal in organic thin-film transistors," Applied Physics Letters, vol. 88, No. 23, pp. 233509-233509-3, Jun. 2006.

Park, et al., "Hybrid silicon evanescent laser fabricated with a silicon waveguide and III-V offset quantum wells", Optics Express, Nov. 14, 2005 / vol. 13, No. 23.

Tizazu, et al., "Photopatterning, Etching, and Derivatization of Self-Assembled Monolayers of Phosphonic Acids on the Native Oxide of Titanium", Langmuir, 2009, 25 (18), pp. 10746-10753.

Tan, et al., "Self-assembled organic thin films on electroplated copper for prevention of corrosion", Journal of Vacuum Science & Technology A: Vacuum, Surfaces, and Films, Jul. 2004, vol. 22, Issue 4, pp. 1917-1925.

Polonsky, et al., "Nanopore in metal-dielectric sandwich for DNA position control," Applied Physics Letters, American Institute of Physics, vol. 91, No. 15, Oct. 18, 2007.

Lin, et al., "Positioning of extended individual DNA molecules on electrodes by non-uniform AC electric fields," Nanotechnology, IOP, vol. 16, No. 11, No. 1, 2005.

D. J. Branton et al., "The potential and challenges of nanopore sequencing," Nature biotechnology, vol. 26, No. 10, 2008, pp. 1146-1153.

K. Jo et al. "A single molecule barcoding system using nanoslits for DNA analysis." PNAS vol. 104, No. 8, 2007, pp. 2673-2678.

D. J. Bonnthuis et al., "Conformation and dynamics of DNA confined in slitlike nanofluidic channels," Phys. Rev. Lett., vol. 101, 2008, pp. 108303-108306.

J. J. Kasianowicz et al., "Characterization of Individual Polynucleotide Molecules Using a Membrane Channel," Proc. Natl. Acad. Sci. USA, vol. 93, 1996, pp. 13770-13773.

Z. Zou et al., "Functionalized nano interdigitated electrodes arrays on polymer with integrated microfluidics for direct bio-affinity sensing using impedimetric measurement," Sensors and Actuators A 136, 2007, pp. 518-526.

D. Fologea et al., "Slowing DNA Translocation in a Solid-State Nanopore," American Chemical Society, Nano Letters, 2005, pp. 1734-1737, vol. 5, No. 9.

J. Lagerqvist et al., "Fast DNA Sequencing via Transverse Electronic Transport," American Chemical Society, Nano Letters, 2006, pp. 779-782, vol. 6, No. 4.

* cited by examiner

FORMING AN ELECTRODE HAVING REDUCED CORROSION AND WATER DECOMPOSITION ON SURFACE USING A CUSTOM OXIDE LAYER

GOVERNMENT RIGHTS

This invention was made with Government support under Contract No.: 1R01HG005110-01 awarded by the National Institute of Health. The Government may have certain rights in this invention.

CROSS-REFERENCE TO RELATED APPLICATIONS

This application is related to U.S. patent application Ser. No. 20080187915 filed Feb. 2, 2002, U.S. patent application Ser. No. 2010025249 filed Aug. 13, 2009, entitled "FORMING AN ELECTRODE HAVING REDUCED CORROSION AND WATER DECOMPOSTION ON SURFACE USING AN ORGANIC PROTECTIVE LAYER" filed on Jun. 22, 2010 having Ser. No. 12/820543, entitled "REDUCING CORROSION AND WATER DECOMPOSITION ON A SURFACE OF A TITANIUM NITRIDE ELECTRODE" filed on Jun. 22, 2010 having Ser. No. 12/820574, the contents of which are incorporated herein by reference.

BACKGROUND OF THE INVENTION

The field of the present invention relates generally to thin film electrodes and, more particularly, to forming an electrode having reduced corrosion and water decomposition on the surface of the electrode.

Electrochemical corrosion of an electrode causes deterioration of the electrode and reduced functionality. Further, if the electrode is immersed in an aqueous solution and a voltage is applied, then water decomposes forming oxygen and hydrogen bubbles on the surface of an electrode.

Protecting surfaces against corrosion by coating such surfaces with an inert substance is known. The protective coating can be a layer of a metal with better protection properties than the bulk material, for example, covering iron or unalloyed steal with a layer of treated zinc. A second option is the protective coating can be an enamel layer or glass-like layer of an inorganic non-metallic material. The third option for corrosion protection is coating with an organic polymer, for example, intrinsically conducting polymers. There is a need for an improved method of inhibiting electrochemical corrosion and water decomposition on electrode surfaces.

BRIEF SUMMARY OF THE INVENTION

Accordingly, the present invention provides a method of forming an electrode having reduced corrosion and water decomposition on a surface thereof. A conductive layer is deposited on a substrate. The conductive layer is partially oxidized by an oxygen plasma process to convert a portion thereof to an oxide layer thereby forming the electrode. The oxide layer is free of surface defects and the thickness of the oxide layer is from about 0.09 nm to about 10 nm and ranges therebetween, controllable with 0.2 nm precision.

DETAILED DESCRIPTION OF THE INVENTION

Thin film electrodes are used in the emerging technology of DNA-Transistors. For a detailed explanation of DNA-Transistors see U.S. Patent Application 20080187915 and U.S. Patent Application 2010025249, both incorporated herein by reference.

Figure 1:
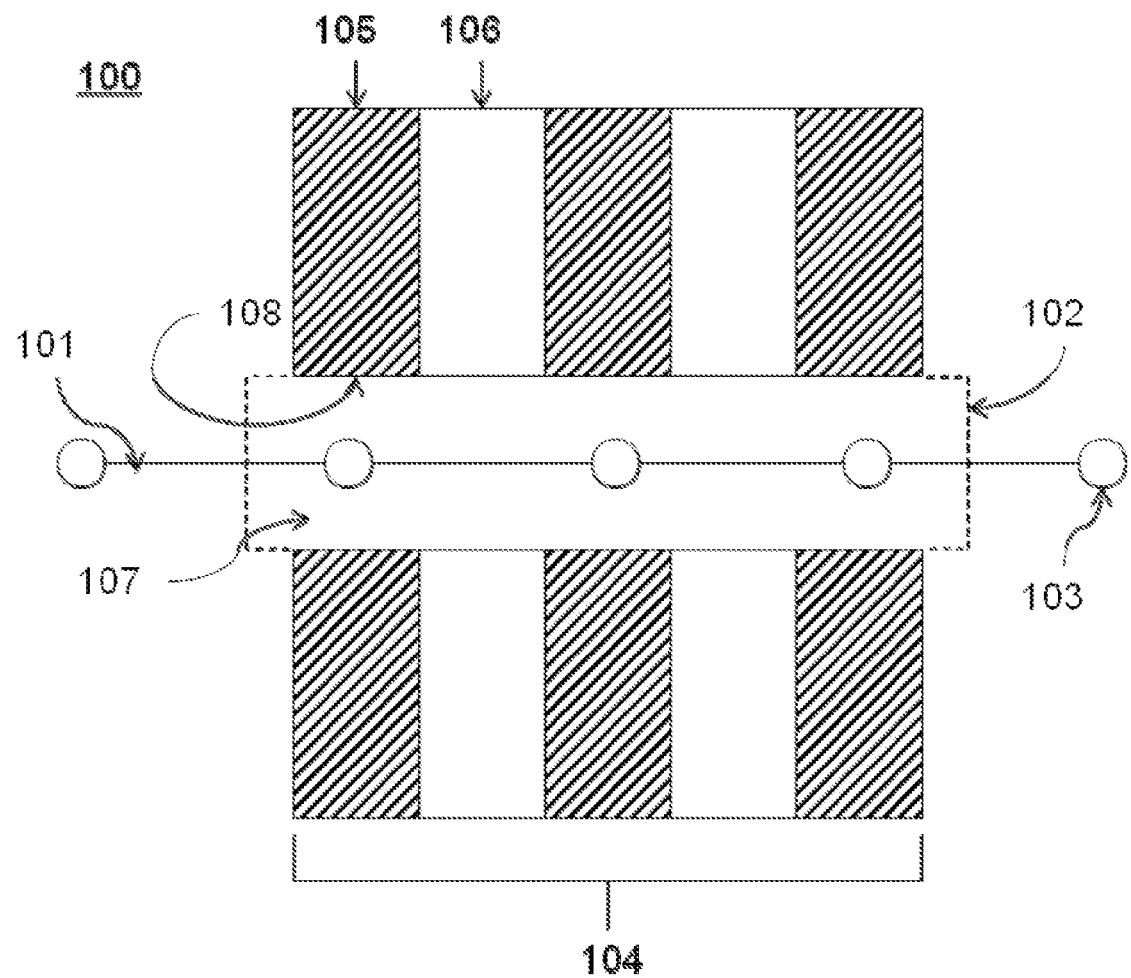
FIG. 1 shows a diagram of a DNA-Transistor device.

FIG. 1 shows a diagram of a DNA-Transistor device 100. The device 100 is capable of controlling the position of a DNA molecule 101 inside a nanopore 102 with single nucleotide accuracy. The device uses the interaction of charges 103 along the backbone of a DNA molecule 101 with an electric field created inside the nanopore 102. The nanopore 102 is drilled through a rack structure 104 of conductive layers 105 and dielectric layers 106 and then wetted with a solvent-electrolyte solution 107 carrying the DNA molecules 101. The surface areas of the conductive layers that are exposed to the solution 107 inside the nanopore 102 serve as electrodes 108 for generating and controlling the electric fields inside the nanopore 102. Voltages applied to the conductive layers 105 in the rack structure 104 allow for trapping and moving the DNA molecule 101 in the nanopore 102.

It is essential for maintaining functionality of the DNA-Transistor device 100 that the nanopore 102 dimensions are not spatially altered and continuous solution 107 flow inside the pore is not compromised during device operation. Specifically, this means that corrosion of the electrode 108 surface areas inside the nanopore 102 must be reduced and water decomposition catalyzed on the surface areas of electrodes 108 must be reduced.

Figure 2:
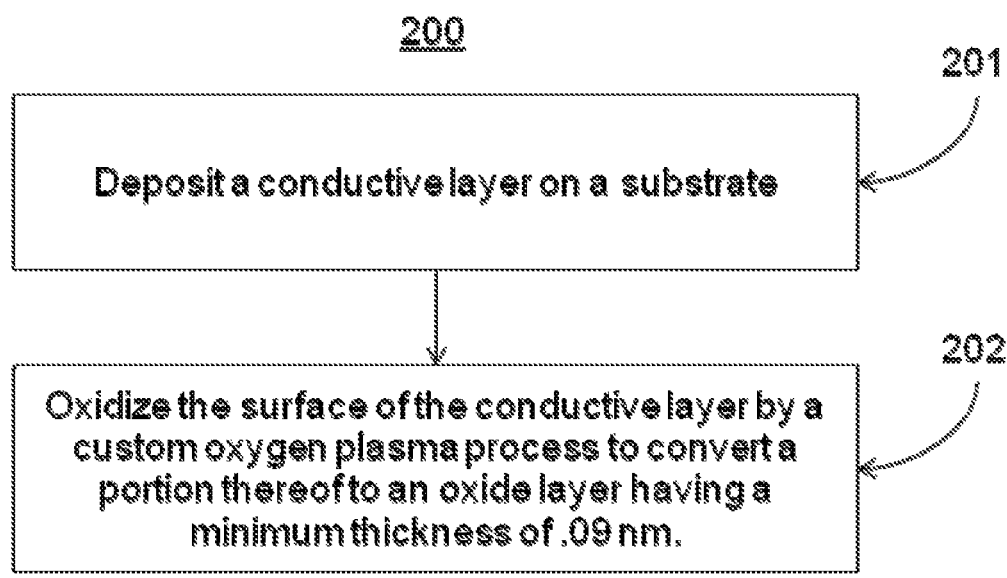
FIG. 2 shows a flow chart for a method of forming an electrode having reduced corrosion and water decomposition on a surface thereof according to an embodiment of the present invention.

FIG. 2 shows a flow chart for a method 200 of forming an electrode having reduced corrosion and water decomposition on a surface thereof according to an embodiment of the present invention. In step 201 a conductive layer is deposited on a substrate. In step 202 the conductive layer is oxidized by a custom oxygen plasma process to convert a portion thereof to an oxide layer.

Figure 3:
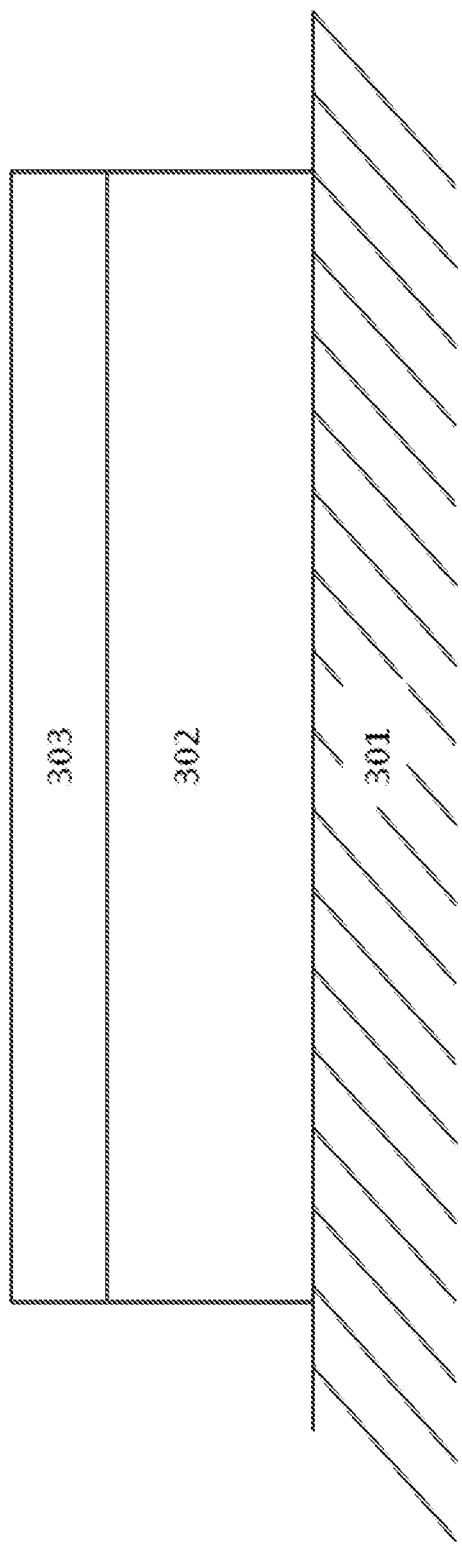
FIG. 3 shows a diagram of the electrode formed as a result of the method of an embodiment of the present invention.

FIG. 3 shows a diagram of the electrode formed as a result of the method of an embodiment of the present invention. The substrate 301 serves as the medium onto which the conductive layer 302 is deposited. The custom oxygen plasma process oxidizes a portion of the conductive layer 302 into an oxide layer 303.

The substrate 301 can be any type of common substrate material such as Kapton, silicon, amorphous hydrogenated silicon, silicon carbide (SiC), silicon dioxide ($SiO_2$), quartz, sapphire, glass, metal, diamond-like carbon, hydrogenated diamond-like carbon, gallium nitride, gallium arsenide, germanium, silicon-germanium, indium tin oxide, boron carbide, boron nitride, silicon nitride ($Si_3N_4$), alumina ($Al_2O_3$), cerium(IV) oxide ($CeO_2$), tin oxide ($SnO_2$), zinc titanate (Zn-$TiO_2$), AlGaAs, CN, InP, GaP, $In_{0.53}Ga_{0.47}As$, chalcogenides, a plastic material and a combination thereof.

The conductive layer 302 can be a metal, semiconductor or a doped semiconductor. Preferably, the conductive layer is titanium nitride; however, other conductive materials can be used. The conductive layer 302 can be a metal such as platinum, rhodium, gold, silver, zinc, titanium, ruthenium and aluminum. The conductive layer 302 can be a semiconductor such as GaAs, AlGaAs, NC, Ge, SiGe, InP, GaP, GaN, $In_{0.53}Ga_{0.47}As$ and chalcogenides. The chalcogenide can be a compound of a metal such as Ge, Sn, Pb, Sb, Bi, Ga, In, Tl and a combination thereof and a chalcogen such as S, Se, Te and a combination thereof. The conductive layer 105 can also be a doped semiconductor such as aluminum doped zinc oxide, phosphorus doped silicon, boron doped silicon, lanthanum doped zirconium dioxide, scandium doped zirconium dioxide, and yttrium doped zirconium dioxide. The conductive layer 302 can be deposited by any deposition process such as sputtering, molecular beam epitaxy, ion beam lithography and atomic layer deposition.

The custom oxygen plasma process uses a working pressure of 150 mT, an oxygen flow rate of 100 sccm, a power of 40-200 W and a time of 0-80 seconds. The custom process provides a uniform oxide layer 303 free of surface defects. The thickness of the oxide layer 303 can be reduced to a thickness of 0.09 nm with a precision of 0.2 nm. It is beneficial that the oxide layer 303 be ultra-thin and highly uniform in application inside a nanopore. The custom oxygen plasma process can be applied not only to planar surfaces but also to topographically patterned surfaces isotropically oxidizing angled and vertical sidewalls as found inside a nanopore.

Figure 4:
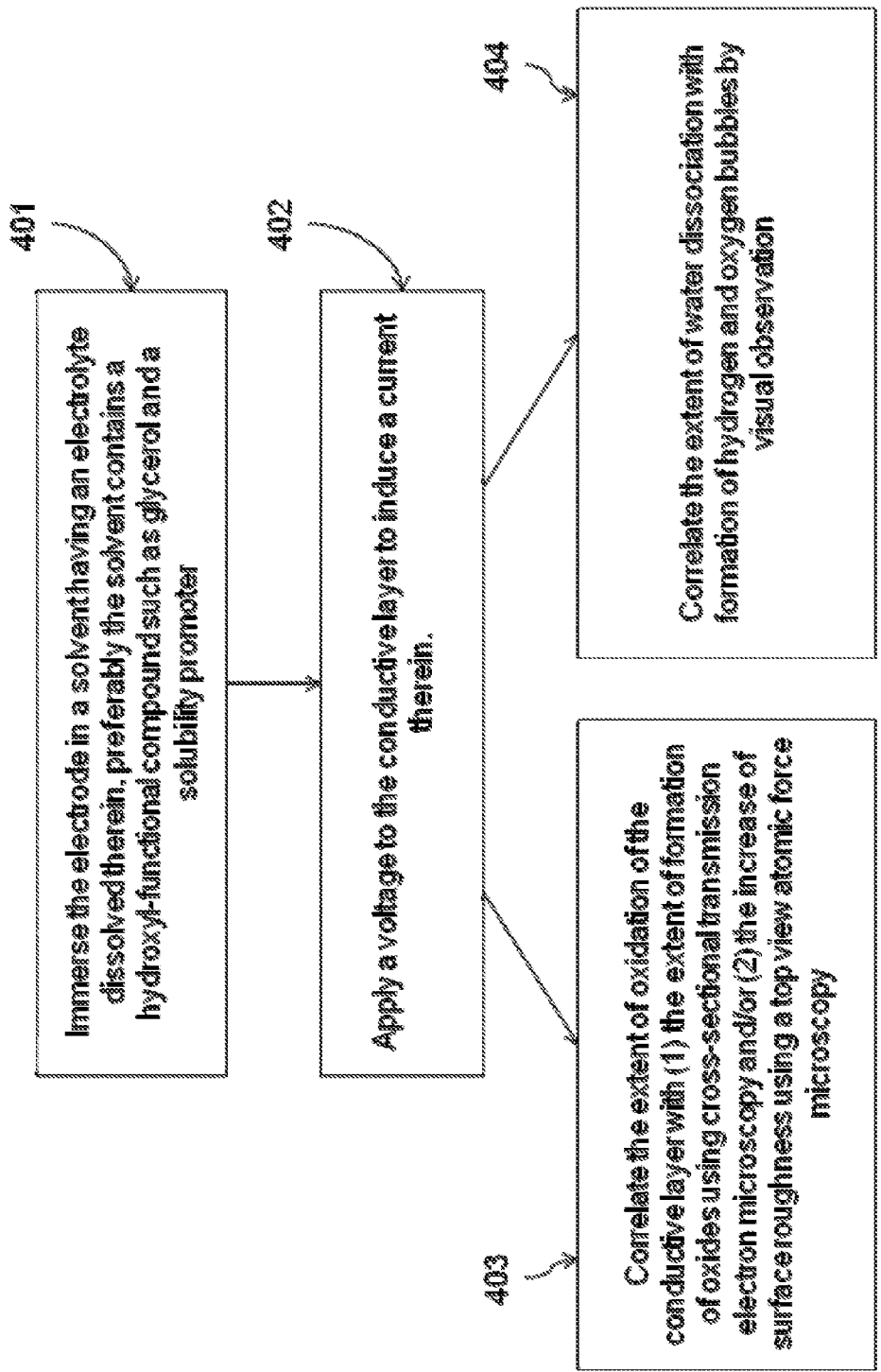
FIG. 4 shows a flow chart for a method of inhibiting corrosion and water decomposition on an electrode surface according to an embodiment of the present invention.

FIG. 4 shows a flow chart for a method of inhibiting corrosion and water decomposition on an electrode surface according to an embodiment of the present invention.

In step 401 the electrode is immersed in a solvent having an electrolyte dissolved therein. In order to inhibit corrosion and water decomposition, the solvent contains a hydroxyl-functional compound such as a linear, branched, or cyclic alcohol of 1 to 6 carbon atoms, ethylene glycol, propylene glycol, butane diol, pentane diol, hexan diol, polyethylene glycol, glycerol, trimethylol ethane, trimethylol propane, isomers thereof, aqueous solutions thereof, and mixtures any of the preceding hydroxyl-functional compounds. Preferably, the solution containing hydroxyl-functional compound has a viscosity from about 1 centi Stokes (cSt) to about 250 centi Stokes.

Further, preferably the solvent also contains a solubility promoter such as dimethylsulfoxide, N,N-dimethylformaide, N,N-dimethylacetamaide, tri(dimethylamino)phosphine, tri(dimethylamino)phosphoramide, ethyl acetate, diethyl ether, methyl ethyl ketone, methoxyethyl acetate, methoxypropyl acetate, methylene chloride, acetone, and mixtures thereof.

The electrolyte dissolved in the solvent can be a salt, an ammonium salt, a quaternary ammonium salt, a substantially dissociated compound, ionic liquids, and mixtures thereof. The electrolyte is preferably at a concentration from about 0.001 weight percent to about 10 weight percent.

In step 402 a voltage is applied to the conductive layer to induce a current therein. The current can be either AC or DC current.

In step 403 the extent of oxidation of the conductive layer is measured. Preferably, this is carried out by using cross-sectional transmission electron microscopy, cross-section scanning electron microscopy and/or using a top view atomic force microscopy.

In step 404 the extent of water dissociation is measured by visually observing the formation of hydrogen and oxygen bubbles.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A method of forming an electrode having reduced water decomposition on a surface thereof, the method comprising:
   depositing a conductive layer on a substrate;
   partially oxidizing said conductive layer by an oxygen plasma process to convert a portion thereof to an oxide layer thereby forming said electrode having reduced corrosion, wherein the oxygen plasma process uses a working pressure of 150 mtorr, an oxygen flow rate of 100 standard cubic centimeters per minute (sccm), and a power of 40-200 watts (W);
   contacting the oxide layer with a solution of an organic surface active compound to form a protective layer on the oxide layer to reduce corrosion and water decomposition;
   wherein said oxide layer is uniformly formed on the substrate and free of surface defects and thickness of said oxide layer is from about 0.09 nm to about 10 nm and ranges therebetween, controllable with 0.2 nm precision;
   immersing said electrode into a solution containing a hydroxyl-functional compound; and
   applying a voltage to said conductive layer.

2. The method of claim 1, wherein said conductive layer comprises a material selected from the group consisting of a metal, semiconductor, and a doped semiconductor.

3. The method of claim 2, wherein said metal is selected from the group consisting of: titanium nitride, platinum, rhodium, gold, silver, zinc, titanium, ruthenium and aluminum.

4. The method of claim 2, wherein said semiconductor is selected from the group consisting of: GaAs, AlGaAs, NC, Ge, SiGe, InP, GaP, GaN, and $In_{0.53}Ga_{0.47}As$ and chalcogenides.

5. The method of claim 4, wherein said metal chalcogenide comprises a metal selected from the group consisting of: Ge, Sn, Pb, Sb, Bi, Ga, In, Tl, and a combination thereof and a chalcogen selected from the group consisting of: S, Se, Te and a combination thereof.

6. The method of claim 2, wherein said doped semiconductor is selected from the group consisting of: aluminum doped zinc oxide, phosphorus doped silicon, boron doped silicon, lanthanum doped zirconium dioxide, scandium doped zirconium dioxide, and yttrium doped zirconium dioxide.

7. The method of claim 1, wherein said conductive layer is deposited by a method selected from the group consisting of: sputtering, molecular beam epitaxy, ion beam lithography, and atomic layer deposition.

8. The method of claim 1, wherein a current is applied to said conductive layer.

9. The method of claim 8, wherein said current is selected from the group consisting of AC and DC currents.

10. The method of claim 1, wherein said substrate is selected from the group consisting of:
Kapton, silicon, amorphous hydrogenated silicon, silicon carbide (SiC), silicon dioxide ($SiO_2$), quartz, sapphire, glass, metal, diamond-like carbon, hydrogenated diamond-like carbon, gallium nitride, gallium arsenide, germanium, silicon-germanium, indium tin oxide, boron carbide, boron nitride, silicon nitride ($Si_3N_4$), alumina ($Al_2O_3$), cerium(IV) oxide ($CeO_2$), tin oxide ($SnO_2$), zinc titanate ($ZnTiO_2$), AlGaAs, CN, InP, GaP, $In_{0.53}Ga_{0.47}As$, chalcogenides, a plastic material and a combination thereof.

11. The method of claim 1, wherein said conductive layer comprises a plurality of same or different individual conductive layers forming a rack.

12. The method of claim 11, wherein said rack is interrupted by at least one dielectric layer.

13. The method of claim 12, further comprising:
drilling a nanopore through said rack to create an exposed surface of said conductive layer prior to said partially oxidizing step.

14. The method of claim 13, wherein said nanopore has a diameter which:
(i) is sufficiently large to allow a width of a DNA molecule move through said nanopore; but
(ii) is sufficiently small to control a position of said DNA mole inside said nanopore.

15. The method of claim 1, wherein said oxide layer has a thickness from about 0.09 nm to about 1.0 nm.

16. The method of claim 15, wherein said oxide layer has a thickness from about 0.09 nm to about 0.6 nm.

17. The method of claim 16, wherein said oxide layer is a monolayer.

18. The method of claim 1, wherein a current is applied to said conductive layer.

19. The method of claim 18, wherein said current is selected from the group consisting of: AC and DC currents.

20. The method of claim 1, wherein said hydroxyl-functional compound is selected from the group consisting of: a linear, branched, or cyclic alcohol of 1 to 6 carbon atoms, ethylene glycol, propylene glycol, butane diol, pentane diol, hexan diol, polyethylene glycol, glycerol, trimethylol ethane, trimethylol propane, isomers thereof, aqueous solutions thereof, and mixtures any of the preceding hydroxyl- functional compounds.

21. The method of claim 20, wherein said hydroxyl-functional compound further comprises a solubility promoter selected from the group consisting of: dimethylsulfoxide, N,N-dimethylformaide, N,N-dimethylacetamaide, tri(dimethylamino)phosphine, tri(dimethylamino)phosphoramide, ethyl acetate, diethyl ether, methyl ethyl ketone, methoxyethyl acetate, methoxypropyl acetate, methylene chloride, acetone, and mixtures thereof.

22. The method of claim 20, further comprising dissolving an electrolyte in said solution containing a hydroxyl-functional compound.

23. The method of claim 22, wherein said electrolyte is a salt, an ammonium salt, a quaternary ammonium salt, a substantially dissociated compound, ionic liquids, and mixtures thereof.

24. The method of claim 23, wherein said electrolyte is at a concentration from about 0.001 weight percent to about 10 weight percent.

25. The method of claim 23, wherein said solution containing a hydroxyl-functional compound has a viscosity from about 1 centi Stokes (cSt) to about 250 centi Stokes.

26. The method of claim 1, further comprising:
applying a voltage to said conductive layer; and
correlating at least one of:
(i) extent of further oxidation of a titanium nitride conductive layer with
(ii) extent of formation of oxides of titanium nitride using cross-sectional transmission electron microscopy; extent of further oxidation of said titanium nitride conductive layer with increase of surface roughness of said conductive layer using top view atomic force microscopy; and
(iii) water decomposition with formation of hydrogen and oxygen bubbles by visual observation.

27. A method of forming an electrode having reduced water decomposition on a surface thereof, the method comprising:
depositing a conductive layer on a substrate;
partially oxidizing said conductive layer by an oxygen plasma process to convert a portion thereof to an oxide layer thereby forming said electrode having reduced corrosion, wherein the oxygen plasma process uses a working pressure of 150 mtorr, an oxygen flow rate of 100 standard cubic centimeters per minute (sccm), and a power of 40-200 watts (W);
contacting the oxide layer with a solution of an organic surface active compound to form a protective layer on the oxide layer to reduce corrosion and water decomposition; and
wherein said oxide layer is free of surface defects and thickness of said oxide layer is from about 0.09 nm to about 10 nm and ranges therebetween, controllable with .2 nm precision.

* * * * *